US00PP18776P2

(12) United States Plant Patent
Trees

(10) Patent No.: US PP18,776 P2
(45) Date of Patent: Apr. 29, 2008

(54) ***LOBELIA* PLANT NAMED 'BALWATAZMI'**

(50) Latin Name: *Lobelia×hybrida*
Varietal Denomination: Balwatazmi

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/602,630

(22) Filed: Nov. 20, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Lobelia* plant named 'Balwatazmi', characterized by its light blue and white bicolored flowers, medium green-colored foliage, and vigorous, upright-mounded growth habit.

1 Drawing Sheet

Latin name of genus and species of plant claimed: *Lobelia×hybrida.*
Variety denomination: 'Balwatazmi'.

BACKGROUND OF THE INVENTION

The present invention relates to a new and distinct cultivar of *Lobelia* plant botanically known as *Lobelia×hybrida* and hereinafter referred to by the cultivar name 'Balwatazmi'.

The new cultivar originated in a controlled breeding program in Arroyo Grande, Calif. during August 2002. The objective of the breeding program was the development of *Lobelia* cultivars with unique flower coloration and a vigorous, mounded, and semi-trailing growth habit.

The new *Lobelia* cultivar is the result of open-pollination. The female (seed) parent of the new cultivar is the proprietary *Lobelia valida* breeding selection designated LOB-133, not patented, characterized by dark lavender-blue and white bicolored flowers, dark green-colored foliage, and upright, poorly-branched growth habit. The male (pollen) parent of the new cultivar is unknown, but is from a group of plants that includes *Lobelia erinus* and *Lobelia×hybrida* plants. The new cultivar was discovered and selected as a single flowering plant within the progeny of the above stated open-pollination during January 2003 in a controlled environment at Arroyo Grande, Calif.

Asexual reproduction of the new cultivar by terminal stem cuttings since January 2003 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balwatazmi' as a new and distinct cultivar of *Lobelia* plant:

1. Light blue and white bicolored flowers;
2. Medium green-colored foliage; and
3. Vigorous, upright-mounded growth habit.

Plants of the new cultivar differ from plants of the female parent primarily in flower color and growth habit.

Of the many commercially available *Lobelia* cultivars known to the inventor, the most similar in comparison to the new cultivar is Periwinkle Blue Improved 'Balobperiblu', U.S. Plant Pat. No. 17,077. However, in side by side comparisons, plants of the new cultivar differ from plants of 'Balobperiblu' in the following characteristics:

1. Plants of the new cultivar are shorter than plants of 'Balobperiblu';
2. Plants of the new cultivar have shorter and wider leaves than plants of 'Balobperiblu';
3. Plants of the new cultivar have a shorter central internode than plants of 'Balobperiblu'; and
4. Plants of the new cultivar have a flower color different from plants of 'Balobperiblu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balwatazmi'. The plants were grown in 4.5 inch pots for 8 weeks in a greenhouse at West Chicago, Ill.

DETAILED BOTANICAL DESCRIPTION

Figure 1:
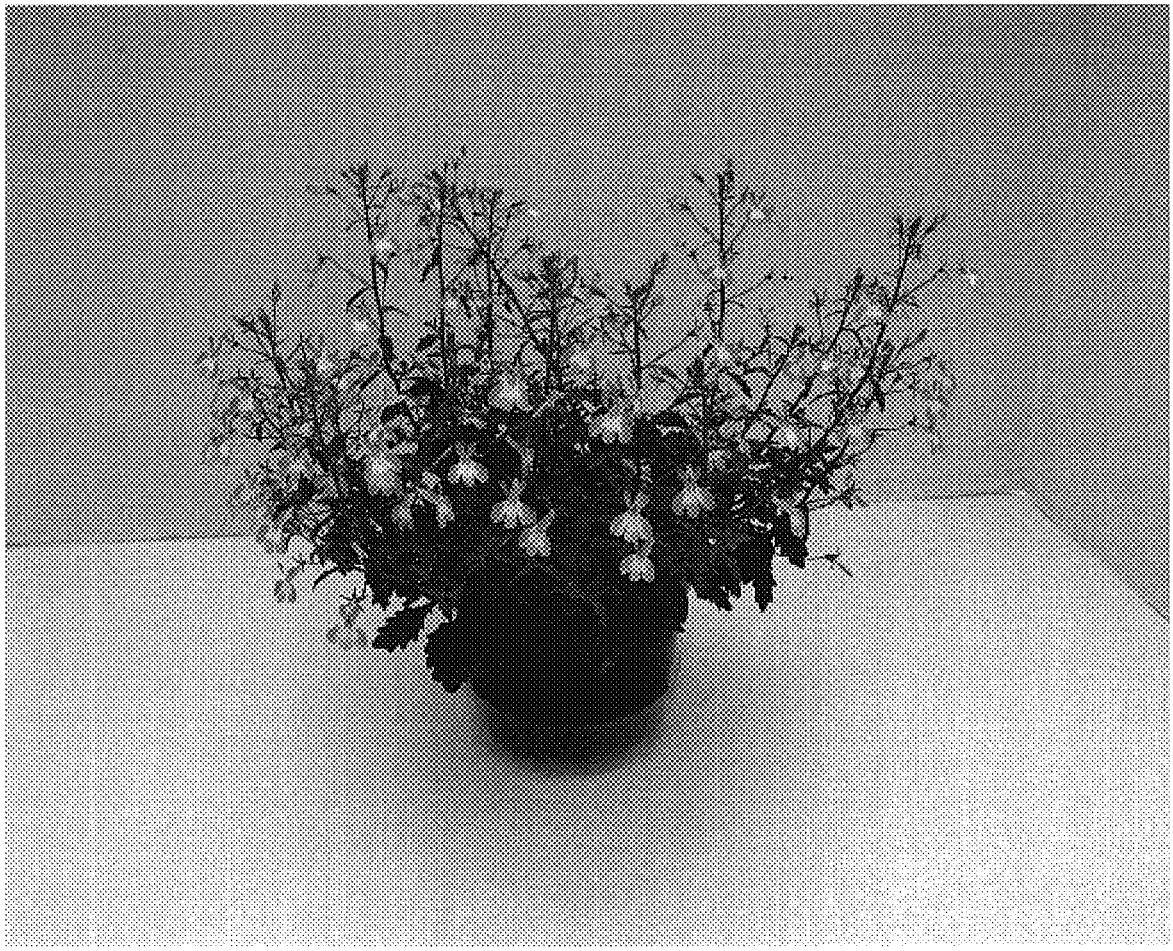
FIG. 1 illustrates a side view of the overall growth and flowering habit of 'Balwatazmi'.
Figure 2:
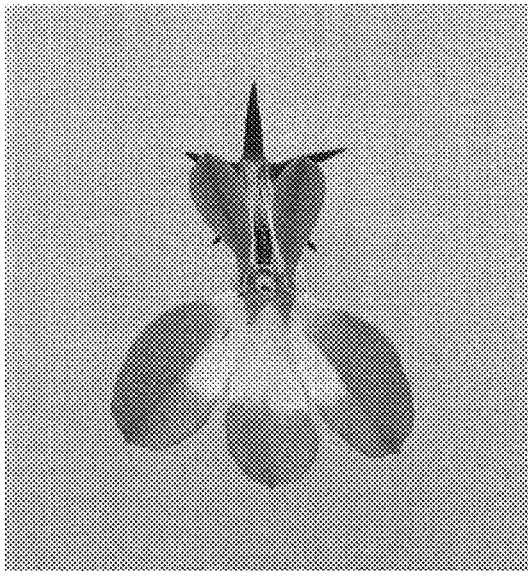
FIG. 2 illustrates a close-up view of an individual flower of 'Balwatazmi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 16, 2006 between 2:00 p.m. and 4:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Lobelia×hybrida* cultivar Balwatazmi.

Parentage:

*Female parent.*—Proprietary *Lobelia valida* breeding selection designated LOB-133, not patented.

*Male parent.*—Unknown.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fine, fibrous.

*Rooting habit.*—Freely branching.

Plant description:

*Commercial crop time.*—Approximately 8 to 10 weeks from a rooted cutting.

*Growth habit and general appearance.*—Vigorous, upright-mounded.

*Size.*—Height from soil level to top of plant plane: Approximately 17.4 cm. Width: Approximately 33.1 cm.

*Branching habit.*—Freely basal branching. Quantity of main branches per plant: Approximately 12.

*Branch.*—Shape: Square. Strength: Strong. Length: Approximately 21.1 cm. Diameter: Approximately 2.0 mm. Length of central internode: Approximately 1.5 cm. Texture: Glabrous. Color of young and mature stems: Closest to 137A.

Foliage description:

*General description.*—Quantity of leaves per main branch: Approximately 14. Fragrance: None. Form: Simple. Arrangement: Alternate.

*Lower leaves.*—Aspect: Acute angle to stem. Shape: Obovate. Margin: Crenate. Apex: Rounded. Base: Attenuate. Venation pattern: Pinnate. Length of mature leaf: Approximately 2.8 cm. Width of mature leaf: Approximately 2.0 cm. Texture of upper and lower surfaces: Glabrous. Color of upper surface of young and mature foliage: 137A with venation of 138B. Color of lower surface of young and mature foliage: 138B with venation of 138C.

*Lower leaf petiole.*—Length: Approximately 6.7 mm. Diameter: Approximately 2.5 mm. Texture: Glabrous. Color of upper surface: 137A with venation of 138B. Color of lower surface: 138B with venation of 138C.

*Upper leaves.*—Aspect: Obtuse angle to stem. Shape: Linear. Margin: Entire. Apex: Mucronate. Base: Sessile. Venation pattern: Pinnate. Length of mature leaf: Approximately 1.4 cm. Width of mature leaf: Approximately 2.6 mm. Texture of upper and lower surfaces: Glabrous. Color of upper surface of young and mature foliage: 137A with venation of 138B. Color of lower surface of young and mature foliage: 138B with venation of 138C.

Flowering description:

*Flowering habit.*—'Balwatazmi' is freely flowering under outdoor growing conditions with substantially continuous blooming from spring through autumn and year-round in greenhouse environment.

*Lastingness of individual flower on the plant.*—Approximately 13 to 15 days.

Inflorescence description:

*General description.*—Type: Loose raceme. Quantity per plant: Approximately 19. Fragrance: None. Length or height: Approximately 9.5 cm. Width: Approximately 6.6 cm. Quantity of fully open flowers per inflorescence: Approximately 7.

Flower description:

*Type.*—Solitary, zygomorphic, bilabiate. Flowers are resupinate because of a half twist in the pedicel.

*Bud.*—Rate of opening: Generally takes 2 to 3 days for bud to progress from first color to fully open flower.

*Bud just before opening.*—Shape: Oblong. Length: Approximately 9.4 mm. Diameter at apex: Approximately 3.0 mm. Diameter at base: Approximately 2.0 mm. Texture: Glabrous. Color: 145D with streaks of 101C.

*Corolla.*—Shape: Bilabiate having an upper lip of two narrow petals and a lower lip of three petals. Petals are fused at the base forming a tube that is split between the two upper petals. Width: Approximately 1.4 cm. Length: Approximately 1.5 cm. Depth: Approximately 1.7 cm.

*Upper petals.*—Quantity: 2. Shape: Oblanceolate. Margin: Entire. Apex: Mucronate. Length: Approximately 6.0 mm. Width: Approximately 2.0 mm. Texture of upper and lower surfaces: Glabrous. Color of upper surface when fully open: Closest to 100B. Color of lower surface when fully open: Closest to 100C.

*Lower petals.*—Quantity: 3, fused for lower third of length. Shape: Obovate. Margin: Entire. Apex: Mucronate. Length: Approximately 9.0 mm. Width: Approximately 5.0 mm. Texture of upper and lower surfaces: Glabrous. Color of upper surface when fully open: Lower two-thirds of central petal is purer white than 155D with a central spot of 100B, upper one-third is closest to 100B. Lower two-thirds of the lengthwise inner-half of lateral petals are purer white than 155D with a central spot of 100B; upper one-third of lengthwise inner-half and the lengthwise outer-half are closest to 100B. At base where petals are fused is N144A. Color of lower surface when fully open: Lower two-thirds of central petal is N155A; upper one-third is closest to 100D. Lower two-thirds of the lengthwise inner-half of lateral petals are N155A; upper one-third of lengthwise inner-half and the lengthwise outer-half are closest to 100D. At base where petals are fused is N144D.

*Corolla tube.*—Length: Approximately 7.6 mm. Diameter at base: Approximately 2.0 mm. Diameter at throat: Approximately 3.0 mm. Texture of inner surface: Pubescent. Texture of outer surface: Glabrous. Color of inner surface: Purer white than 155D with spots of 100B and two streaks of N144A extending from the region where the lower petals fuse. Color of outer surface: N155A with streaks of 100D and two streaks of N144D extending from the region where the lower petals fuse.

*Calyx.*—Shape: Star. Diameter at base: Approximately 1.0 mm. Diameter at petals: Approximately 9.8 mm.

*Sepals.*—Quantity per flower: 5, fused at base. Shape: Lanceolate. Apex: Acute. Length: Approximately 4.0 mm. Width: Approximately 1.0 mm. Texture of upper and lower surfaces: Glabrous. Color of upper and lower surfaces: 137A.

*Pedicel.*—Strength: Strong, flexible. Aspect: Twisted, acute angle to stem. Length: Approximately 2.1 cm. Diameter: Approximately 1.0 mm. Texture: Glabrous. Color: 144A.

*Reproductive organs.*—Androecium: Stamen quantity: 5 per flower, anthers and upper half of filaments connate. Filament length: Approximately 5.0 mm. Filament texture: Glabrous. Filament color: Closest to 100A at anther transitioning to N155A at base. Anther shape: Linear. Anther length: Approximately 2.0 mm. Anther color: 103A. Pollen amount: Moderate. Pollen color: 155D. Gynoecium: Pistil quantity: 1 per flower. Pistil length: Approximately 1.0 cm. Stigma shape: Bilobed, ovoid. Stigma width: Approximately 1.0 mm. Stigma color: 86A. Style length: Approximately 8.0 mm. Style color: 144B. Ovary diameter: Approximately 2.0 mm. Ovary texture: Glabrous. Ovary color: 144A.

Seed and fruit production. Neither seed nor fruit production has been observed.

Disease and pest resistance: Resistance to pathogens and pests common to *Lobelia* has not been observed.

What is claimed is:

1. A new and distinct cultivar of *Lobelia* plant named 'Balwatazmi', substantially as herein shown and described.

* * * * *